United States Patent [19]

Kauffman

[11] Patent Number: 4,764,258
[45] Date of Patent: Aug. 16, 1988

[54] METHOD FOR EVALUATING THE REMAINING USEFUL LIFE OF A HYDROCARBON OIL

[75] Inventor: Robert E. Kauffman, Kettering, Ohio

[73] Assignee: University of Dayton, Dayton, Ohio

[21] Appl. No.: 945,603

[22] Filed: Dec. 23, 1986

[51] Int. Cl.[4] ............................................. G01N 27/52
[52] U.S. Cl. .......................................... 201/1 T; 436/60
[58] Field of Search ..................... 436/60, 61; 204/1 T

[56] References Cited

U.S. PATENT DOCUMENTS

| | | | |
|---|---|---|---|
| 3,003,350 | 10/1961 | Stewart | 73/64 |
| 3,182,255 | 5/1965 | Hopkins et al. | 324/61 P |
| 3,526,127 | 9/1970 | Sarkis | 292/27 |
| 4,029,554 | 6/1977 | Ellison | 204/1 T |
| 4,082,511 | 4/1978 | Bedford | 436/60 |
| 4,317,705 | 3/1982 | Hamada et al. | 204/1 T |

OTHER PUBLICATIONS

Donald T. Sawyer, "Experimental Electrchemistry for Chemists", pp. 329-394, (1974).

Primary Examiner—G. L. Kaplan
Attorney, Agent, or Firm—Biebel, French & Nauman

[57] ABSTRACT

A method is disclosed for measuring the remaining useful life of a hydrocarbon oil containing at least one additive species. An oil sample is mixed with a solvent, a solid substrate, and in some cases an electrolyte to produce an analysis sample. The analysis sample is placed into an electrolytic cell and subjected to a voltammetric analysis, whereby increasing potential is applied to the cell to produce an oxidation reaction and a varying electric current. The current during the voltammetric analysis is measured and recorded. Remaining useful life for the oil is then determined from the oxidation current wave height produced.

32 Claims, 1 Drawing Sheet

METHOD FOR EVALUATING THE REMAINING USEFUL LIFE OF A HYDROCARBON OIL

BACKGROUND OF THE INVENTION

The present invention relates generally to oils, and more specifically, to a method for evaluating a hydrocarbon oil during use to determine its remaining useful life.

It is common to lubricate and cool the components of equipment by wetting them with a hydrocarbon oil lubricant. Such a lubricant experiences various environmental stresses as it carries out such functions that cause its basestock to undergo thermal-oxidative degradation. For this reason, various antioxidants are added to the lubricant to protect its lubricating characteristics. So long as the antioxidant system remains intact, the oxidative degradation of the basestock, and hence the changes in the lubricant's properties, are minimal.

Hydrocarbon oils are also commonly used as transmission fluids and in hydraulic systems. cases, the oil is subjected to pressures, frequent movement and heat. These oils also experience stresses that degrade the basestock, and antioxidants are added to such oils.

In a similar manner, hydrocarbon cooking oils undergo serious thermal stresses. Degradation of the basestock can result in production of acids within the oil which affect the taste of food, and such oils are also protected by an antioxidant system.

Antioxidant species within an oil are gradually depleted with equipment operating time. Eventually, the antioxidants become ineffective, which allows large changes to occur in the physical properties of the oil's basestock. At such point, the oil is no longer capable of adequately carrying out its function, and its useful life ends For lubricants, this can result in excessive component wear and eventual failure of the equipment. For cooking oils, acid concentrations within the oil may increase, affecting the taste of foods fried within the oil.

Since it is undesirable to continue to use an oil beyond the end of its useful life, scheduled oil changes have been devised for various types of equipment. The length of equipment operating time between scheduled changes is selected quite conservatively to ensure that dysfunctional oil is not permitted to remain within the equipment. However, this results in oils with remaining useful life being discarded.

It can therefore be seen that the ability to predict the remaining useful life of an oil would eliminate the need to perform oil changes on the basis of a fixed schedule. This would permit longer use of an oil, thereby providing savings in material and labor costs. Further, abnormal depletion rates for antioxidants within a lubricant or hydraulic fluid sample can detect severe wear problems in operating equipment prior to equipment failures. Abnormal depletion rates in cooking oil can signal improper thermal control within the equipment or other malfunctions.

Various thermal-oxidative and chemical-oxidative stressing techniques having the capability to evaluate remaining useful life are known. However, such techniques are unsuitable for routine use. Thermal-oxidative stressing techniques require the use of high temperatures and pressures and long analysis times in the order of 30 minutes. Chemical oxidative stressing techniques are difficult in operation, require unstable reagents, and also require long analysis times in the order of 120 minutes.

What is needed, therefore, is a method for evaluating the remaining useful life of a hydrocarbon oil which does not require the use of high temperature and pressure or unstable reagents. Such a technique should be rapid, i. e., analysis times of less than a minute, as well as easy to operate and capable of being performed with inexpensive equipment.

SUMMARY OF THE INVENTION

The present invention provides a method for measuring the remaining useful life of an oil, which is specifically adapted to the evaluation of hydrocarbon oils typically used as lubricants, transmission fluids, hydraulic fluids, cooking oils and the like.

The method is used on a hydrocarbon oil containing at least one additive species, and includes mixing an oil sample with a solvent and a solid substrate to produce an analysis sample. The substrate is permitted to settle from the analysis sample, whereupon the analysis sample is placed into an electrolytic cell. An electric potential of a first value is applied to the analysis sample to produce an electric current therethrough. Using a voltammetric technique, the potential is varied from the first value to a second value to produce an oxidation reaction of the additive species within the cell. The current produced during the oxidation reaction is measured and recorded.

The maximum current produced during the oxidation reaction is determined as a measure of remaining useful life.

The additive species may be a substituted phenol antioxidant or an oxidation product of a substituted phenol witn antioxidant capacity. In such a case, the solvent may be ethanol having an inorganic base added thereto. The base can be potassium hydroxide (KOH). The potassium hydroxide is added to the ethanol in an amount of 50 to 100 millimoles per liter of ethanol.

The solid substrate may be sand. The sand is added in an amount of at least 2.0 g of sand to 1.0 ml of oil.

For the substituted pnenol antioxidant and respective oxidation products with antioxidant capacity, the first and second potential values are within the range of $-1.5$ V and $+1.5$ V. Preferably, the first and second potential values are, respectively, $-0.2$ V and $+0.2$ V. The potential is varied at a rate of 0.01 V/sec to 30.0 V/sec, with 1.0 V/sec preferred.

Alternatively, the additive species may be a metal-dithiodiphosphate multi-function additive or an oxidation product of the metal-dithiodiphosphate with antioxidant capacity. In such a case, an electrolyte is mixed into the analysis sample. The solvent may be acetone, and the electrolyte is lithium perchlorate ($LiClO_4$). The addition of up to 1 part of distilled water per 5 parts of solvent may be used to enhance the produced oxidation wave, with 1 part distilled water to 10 parts acetone preferred. The lithium perchlorate may be added to the 1:10 water/acetone solution in an amount of 50 to 100 millimoles per liter of solution.

The solid substrate may be sand or Celite TM 545, which is diatomaceous earth. The substrate is added in an amount of at least 2.0 g of substrate to 1.0 ml of oil.

For the metal-dithiodiphosphate multi-function additive and its oxidation products with antioxidant capacity, the first and second potential values are within the range of $-1.5$ V and $+1.5$ V. Preferably, the first and second potential values are, respectively, $-0.2$ V and 0.9 V. The potential is varied at a rate of 0.01 V/sec to 30.0 V/sec, with 1.0 V/sec preferred.

In either case, the electrolytic cell includes a microelectrode and a reference electrode. The microelectrode may be a glassy carbon electrode, and the reference electrode may be Ag/AgCl. Additional electrodes, auxiliary electrodes, can be added to the electrode system to eliminate the effects of resistive drop for high resistance solutions, and may be platinum wire.

Accordingly, it is an object of the present invention to provide a method of evaluating the remaining useful life of an oil; to provide such a method which is specifically usable in evaluating hydrocarbon oils; to provide such a method which is capable of monitoring antioxidant, antiwear or acid neutralizing additives; to provide such a method which does not require the use of high temperatures and pressures or unstable reagents; to provide such a method which is rapidly performed, with analysis times of less than a minute; to provide such a technique which is easy to operate and can be performed with inexpensive equipment; and to provide such a technique which requires minimal sample preparation and can be used with small sample sizes.

Other objects and advantages of the present invention will be apparent from the following description, the accompanying drawings, and the appended claims.

DETAILED DESCRIPTION OF THE PREFERRED EMBODIMENT

The method for evaluating the remaining useful life of a hydrocarbon oil in accordance with the present invention is based generally upon voltammetric analysis of the lubricant sample. In general, voltammetric techniques are electroanalytic methods wherein a sample to be analyzed is mixed with an electrolyte and a solvent, and placed within an electrolytic cell. Data is obtained by measuring the current passing through the cell as a function of the potential applied, and test results are based upon current, voltage and time relationships at the cell electrodes.

The cell consists of a fluid container into which is mounted a small, easily polarized microelectrode, and a large non-polarizable reference electrode. The reference electrode should be massive relative to the microelectrode so that its behavior remains essentially constant with the passage of small current; that is, it remains unpolarized during the analysis period. Additional electrodes, auxiliary electrodes, can be added to the electrode system to eliminate the effects of resistive drop for high resistance solutions. In performing a voltammetric analysis, the potential across the electrodes rs varied linearly with time, and the resulting current is recorded as a function of the potential.

The present invention is based upon subjecting a sample of hydrocarbon oil to voltammetric analysis. The method can monitor the concentrations of two different classes of additives and their oxidation products wet antioxidant capacities commonly found in such oils: substituted phenols, used as antioxidants; and metal dithiodiphosphates (DTDP), e.g., zinc dithiodiphosphates, having antioxidant, antiwear, and acid neutralizing capabilities. As the increasing voltage is applied to the sample within the cell, the various additive species under investigation within the oil are caused to electrochemically oxidize. The data recorded during this oxidation reaction can then be used to determine the remaining useful life of the oil specimen.

Figure 1:
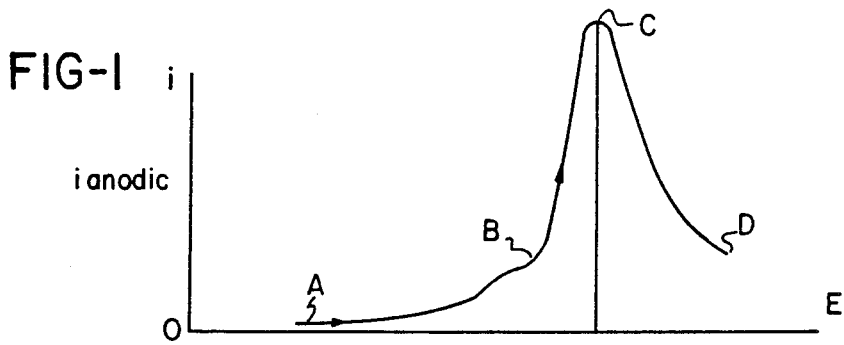
FIG. 1 is a plot illustrating current produced in a lubricant sample as a function of potential applied in practicing the method for evaluating remaining useful life of an oil in accordance with the present invention.

A typical current-potential curve produced during the practice of the present invention can be seen by referenre to FIG. 1. Initially, as shown at point A, the applied potential produces an electrochemical reaction having a rate so slow that virtually no current flows through the cell. As the voltage is increased, shown at point B, the electro-active species, i.e., the substituted phenols or metal-DTDP in the oil, begins to oxidize at the microelectrode surface, producing an anodic rise in the current. As the potential is further increased, the decrease in the electro-active species concentration at the electrode surface and the exponential increase of the oxidation rate lead to a maximum in the current-potential curve shown at point C. The current then decreases to the diffusion-limited anodic current value at point D. The peak so produced is referred to as the oxidation wave.

It has been found that the height of the oxidation wave (point C in FIG. 1) can be used in evaluating the remaining useful life of a hydrocarbon oil. Slight variations in procedure are necessary depending upon whether substituted phenols or metal-DTDP are the additives of interest.

Although any solvent capable of dissolving the required inorganic base and additive of interest can be used, the preferred solvent for use in the evaluation technique for substituted phenols and their oxidation products with antioxidant capacities is ethanol. Solutions containing 50 to 100 millimoles of an inorganic base, preferably potassium hydroxide (KOH), per liter of etnanol are preferred. No electrolyte need be added to the solvent, since the potassium hydroxide itself acts as an electrolyte.

The oil sample to be analyzed is dispensed onto a solid substrate, preferably sand. The use of such a solid substrate is required because the hydrocarbon-based oils are insoluble in ethanol. Consequently, the substrate is coated with the oil basestock and the additives of interest are extracted into solution. The use of a solid substrate is particularly important when used oil samples are analyzed, since such samples also contain oxidation products which interfere with the evaluation response unless removed from solution by the substrate.

Since the oil is extracted out of solution by the solid substrate, any ratio of oil sample amount to solvent amount can be used. The amount of sand is dependent upon the amount of sample used, and the ratio should be greater than 2.0 grams of sand to 1.0 ml of oil.

In one specific example, 200 μl of the oil sample was dispensed onto 2.0 grams of sand. 5.0 ml of a basic (0.1 M KOH) ethanol solution was added, and the liquid/solid mixture was shaken by hand for approximately 15 seconds. The sand coated with the lubricating oil was allowed to settle out prior to analysis.

When the analysis is applied to monitor antioxidants within cooking oil, it is preferred to increase the size of the oil sample to 1.0 ml, rather than the 200 μl used in the case of lubricants. Except for this change, the method is the same for either type of oil.

In monitoring the multi-functional metal-DPDT and their oxidation products with antioxidant capacity, the preferred solvent for use is a 1:10 distilled water/acetone solution, although any solvent capable of dissolving the required electrolyte and additives of interest can be used. The preferred electrolyte for use in the technique is lithium perchlorate (LiClO$_4$), although any soluble electrolyte can be used. The appropriate amount of electrolyte is added to the solvent to produce a solution suitable for voltammetric analysis. Solutions containing 50–100 millimoles of LiClO$_4$ per liter of 1:10 water/acetone solution are preferred.

The solid substrate is preferably comprised of either Celite TM 545, which is diatomaceous earth, or sand. Again, any ratio of oil amount to solvent amount can be used. The amount of solid substrate should be greater than 2.0 grams to 1.0 ml of oil sample.

In one specific example, an electrolyte solution was prepared by dissolving 2.7 g of LiClO$_4$ in 500 ml of acetone. An analysis sample was prepared by dispensing 200 μl of the oil sample onto 2.0 grams of Celite TM 545. 5.0 ml of the acetone solution and 0.5 ml of distilled water were added, and the liquid/solid mixture was shaken by hand for approximately 15 seconds. The Celite TM 545 coated with the lubricating oil was allowed to settle out prior to analysis.

In the electrolytic cell, an Ag/AgCl reference electrode is preferred. Also preferred is a glassy carbon working electrode and a platinum wire auxiliary electrode. Of course, electrodes formed from other materials are also usable.

In carrying out the voltammetric analysis, a single scan of potential increased linearly with time is applied to the analysis sample within the cell. For monitoring substituted phenols and their oxidation products with antioxidant capacities, the voltage is increased from −0.2 to +0.2 volts at 0.01 V/sec to 30.0 V/sec with 1.0 V/sec preferred. For tne multi-functional metal-DPDT and their oxidation products with antioxidant capacity, voltage is increased from −0.2 to +0.9 volts at 0.01 V/sec to 30.0 V/sec with 1.0 V/sec preferred. In either case, the produced oxidation wave is recorded.

Once the voltammetric scan has been performed, the results obtained are analyzed. In the case of substituted phenols and their oxidation products, the natural logarithm of the oxidation wave height is plotted against the operating time of the equipment from which the sample was taken. This data produces linear plots. Thus, the percentage and hours of remaining useful life for each oil can be calculated using the following equations:

$$R_\% = \frac{\ln(H \text{ of sample}) - \ln(H \text{ of 0\% standard})}{\ln(H \text{ of 100\% standard}) - \ln(H \text{ of 0\% standard})}$$

$$DR = \frac{\ln(H \text{ of sample 1}) - \ln(H \text{ of sample 2})}{T_2 - T_1}$$

$$R_H = \frac{\ln(H \text{ of sample}) - \ln(H \text{ of 0\% standard})}{DR}$$

where $R_\%$ is the percentage of useful life remaining, H is the oxidation wave height occurring during the scan, 0% standard is an oil sample taken after the end of its useful life, 100% standard is an oil sample of fresh oil, DR is the oil's depletion rate, T is the equipment operating time at which the sample was obtained, and $R_H$ is the hours of useful life remaining.

In the case of metal-DPDT and their oxidation products, linear plots are obtained by plotting the actual height of the oxidation wave against the operating time of the equipment from which the sample was taken. In this case, the percentage and hours of remaining useful life for the lubricant can be calculated using the following equations:

$$R_\% = \frac{(H \text{ of sample}) - (H \text{ of 0\% standard})}{(H \text{ of 100\% standard}) - (H \text{ of 0\% standard})}$$

$$DR = \frac{(H \text{ of sample 1}) - (H \text{ of sample 2})}{T_2 - T_1}$$

$$R_H = \frac{(H \text{ of sample}) - (H \text{ of 0\% standard})}{DR}$$

where again $R_\%$ is the percentage of useful life remaining, H is the oxidation wave height occurring during the scan, 0% standard :s an oil sample taken after the end of its useful life, 100% standard is an oil sample of fresh oil, DR is the oil's depletion rate, T is the equipment operating time at which the sample was obtained, and $R_H$ is the hours of useful life remaining.

Figure 2:
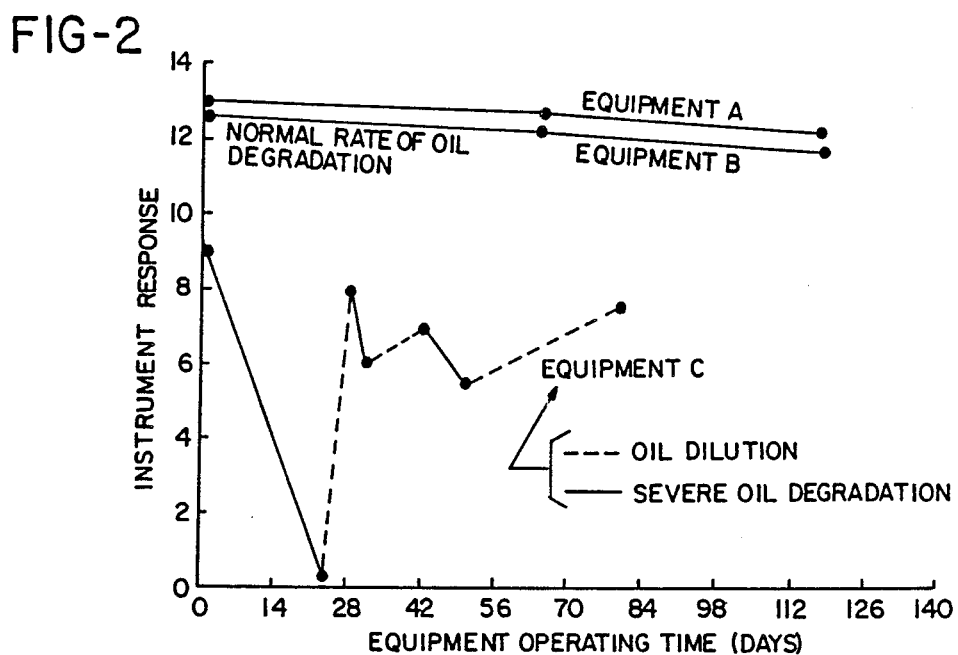
FIG. 2 is a plot illustrating typical results produced by the evaluation method for several pieces of operating equipment.

Typical results obtained with the oil evaluation technique are shown graphically in FIG. 2. Several sample series were taken from three different pieces of operating equipment. Analysis was performed to monitor the Zn-DTDP additives. For equipment A and equipment B, response decreases at a slow, constant rate, indicating normal operation of the equipment. Of course, analyses should be performed on samples of fresh lubricant (100% standard) and lubricant at the ends of its useful life (0% standard) to establish the end points for the plots. However, the plots shown in FIG. 2 demonstrate the capability of the evaluation method.

Oil samples were also taken from equipment C, which was known to be operating in an abnormal manner. The rapid response decrease dramatically illustrates the ability of the evaluation technique to detect improperly operating equipment. It should be noted that the use of fresh oil dilutions within equipment C is also detected by the evaluation technique, represented by increases in instrument response in FIG. 2. The starting points after each oil dilution cannot be established because oil samples taken immediately after the fresh oil dilutions were not obtained.

Figure 3:
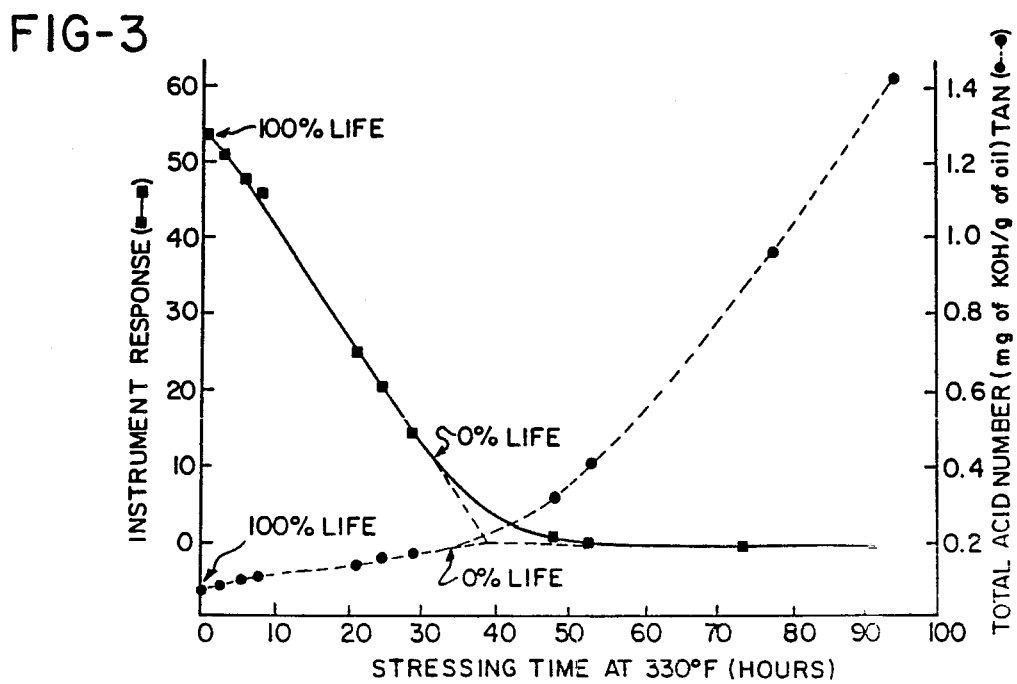
FIG. 3 is a plot illustrating evaluations performed on cooking oil using the evaluation method of the invention and a known chemical analysis technique.

Sample results obtained from evaluating hydrocarbon-based cooking oils can be seen by reference to FIG. 3. Fresh cooking oil was stressed at 330° F, a typical deep fryer temperature, in an open container, and oil samples were taken at 3 to 24 hour intervals. Ihe samples were evaluated chemically by a known method to determine a total acid number for each oil sample as a basis for comparing the evaluation method disclosed herein. The total acid number was plotted versus stressing time to produce the plot shown in broken lines in FIG. 3. The total acid number measurement plot shows a break point (end of useful life) at approximately 35 hours of stressing time. The rapid and continued production of carboxylic acids indicates that the antioxidant system can no longer protect the hydrocarbon basestock from thermaloxidative degradation, and results in the taste of the fried food being adversely affected.

The same cooking oil samples were evaluates using the voltammetric technique described herein for analyzing the substituted phenolic antioxidant additives. The instrument response decreases linearly at a constant rate, departing from such linearity at approximately 35 hours of stressing time, indicating the end of the useful life for the cooking oil. Such results are in agreement with those achieved using the less sensitive and more difficult total acid number evaluation. Thus, the evaluation technique disclosed herein has the potential of determining the remaining useful life of a cooking oil so that the maximum cooking time of the oil can be obtained without affecting the quality of the food.

While the methods herein described constitute preferred embodiments of this invention, it is to be understood that the invention is not limited to these precise methods, and that changes may be made therein without departing from the scope of the invention, which is defined in the appended claims:

What is claimed is:

1. A method for measuring the remaining useful life of a hydrocarbon oil containing an oil basestock and at least one additive species, comprising the steps of:
   mixing an oil sample with a solvent and a solid substrate to produce an analysis sample wherein said basestock coats said substrate;
   permitting said substrate and said basestock coated thereon to settle from said analysis sample;
   placing said analysis sample into an electrolytic cell;
   applying an electric potential of a first value to said analysis sample to produce an electric current therethrough;
   varying said potential from said first value to a second value to produce an oxidation reaction of said additive species within said cell; and
   measuring and recording said current during said oxidation reaction.

2. The method as defined in claim 1, wherein said additive species is a substituted phenol antioxidant or an oxidation product of the substituted phenol with antioxidant capacity.

3. The method as defined in claim 2, wherein said solvent is ethanol having an inorganic base added thereto.

4. The method as defined in claim 3, wherein said inorganic base is potasssium hydroxide (KOH).

5. The method as defined in claim 4, wherein said potassium hydroxide is added to said ethanol in an amount of 50 to 100 millimoles per liter of ethanol.

6. The method as defined in claim 2, wherein said solid substrate is sand.

7. The method as defined in claim 6, wherein said sand is added in an amount of at least 2.0 g of sand to 1.0 ml of said oil.

8. The method as defined in claim 2, wherein said first and second potential values are within the range of $-1.5$ V and $+1.5$ V.

9. The method as defined in claim 8, wherein said first and second potential values are, respectively, $-0.2$ V and $+0.2$ V.

10. The method as defined in claim 9, wherein said potential is varied at a rate of 0.01 V/sec to 30.0 V/sec.

11. The method as defined in claim 9, wherein said potential is varied at a rate of 1.0 V/sec.

12. The method as defined in claim 1, wherein said additive species is a metal-dithiodiphosphate multifunction additive or an oxidation product of the metal-dithiodiphosphate with antioxidant capacity.

13. The method as defined in claim 12, comprising the step of mixing an electrolyte into said analysis sample.

14. The method as defined in claim 13, wherein said solvent contains up to 1 part distilled water per 5 parts of acetone.

15. The method as defined in claim 13, wherein said solvent contains 1 part distilled water per 10 parts acetone.

16. The method as defined in claim 15, wherein said electrolyte is lithium perchlorate ($LiClO_4$).

17. The method as defined in claim 16, wherein said lithium perchlorate is added to the 1:10 water/acetone solution in an amount of 50 to 100 millimoles per liter of solution.

18. The method as defined in claim 12, wherein said solid substrate is sand.

19. The method as defined in claim 12, wherein said substrate is added in an amount of at least 2.0 g substrate to 1.0 ml of said oil.

20. The method as defined in claim 12, wherein said first and second potential values are within the range of $-1.5$ V and $+1.5$ V.

21. The method as defined in claim 20, wherein said first and second potential values are, respectively, $-0.2$ V and $+0.9$ V.

22. The method as defined in claim 21, wherein said potential is varied at a rate of 0.01 V/sec of 30.0 V/sec.

23. The method as defined in claim 21 wherein said potential is varied at a rate of 1.0 V/sec.

24. The method as defined in claim 1, wherein said electrolytic cell includes a microelectrode, a reference electrode, and an auxiliary electrode.

25. The method as defined in claim 24, wherein said microelectrode is a glassy carbon electrode.

26. Tne method as defined in claim 24, wherein said reference electrode is Ag/AgCl.

27. The method as defined in claim 24, wherein said auxiliary electrode is platinum wire.

28. The method as defined in claim 1, comprising the further step of determining the maximum current produced during said oxidation reaction.

29. A method for measuring the remaining useful life of a hydrocarbon oil containing an oil basestock and at least one substituted phenol antioxidant species or an oxidation product of a substituted phenol with antioxidant capacity, comprising the steps of:
   mixing an oil sample with a solvent, an inorganic base and a solid substrate to produce an analysis sample wherein said basestock coats said substrate;
   permitting said substrate and said basestock coated thereon to settle from said analysis sample;
   placing said analysis sample into an electrolytic cell;
   subjecting said analysis sample to a voltammetric analysis, whereby a varying electric current is produced during an oxidation reaction within said cell; and
   measuring and recording said current during said voltammetric analysis.

30. The method as defined in claim 29, comprising the further step of determining a maximum current value during said voltammetric analysis.

31. The method as defined in claim 29, comprising the further step of determining a maximum current value during said voltammetric analysis.

32. A method for measuring the remaining useful life of a hydrocarbon oil containing an oil basestock and at least one metal dithiodiphosphate multi-function species or an oxidation product of a metal dithiodiphosphate with antioxidant capacity, comprising the steps of:

mixing an oil sample with a solvent, an electrolyte and a solid substrate to produce an analysis sample wherein said basestock coats said substrate;
permitting said substrate and said basestock coated thereon to settle from said analysis sample;
placing said analysis sample into an electrolytic cell;
subjecting said analysis sample to a voltammetric analysis, whereby a varying electric current is produced during an oxidation reaction within said cell; and
meausring and recording said current during said voltammetric analysis.

* * * * *